(12) United States Patent
Sun et al.

(10) Patent No.: US 7,353,060 B2
(45) Date of Patent: *Apr. 1, 2008

(54) ADAPTIVE ANTI-TACHYCARDIA THERAPY APPARATUS AND METHOD

(75) Inventors: Weimin Sun, Plymouth, MN (US); Bruce H. KenKnight, Maple Grove, MN (US); Martin Tze, Maplewood, MN (US); Yatheendhar Manicka, Woodbury, MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 553 days.

This patent is subject to a terminal disclaimer.

(21) Appl. No.: 10/953,081

(22) Filed: Sep. 29, 2004

(65) Prior Publication Data

US 2005/0090869 A1    Apr. 28, 2005

Related U.S. Application Data

(63) Continuation of application No. 10/037,622, filed on Jan. 2, 2002, now Pat. No. 6,801,806, which is a continuation of application No. 09/545,945, filed on Apr. 10, 2000, now Pat. No. 6,400,986.

(51) Int. Cl.
*A61N 1/362* (2006.01)

(52) U.S. Cl. ........................................ 607/5
(58) Field of Classification Search ........... 607/5–14
See application file for complete search history.

(56) References Cited

U.S. PATENT DOCUMENTS

| 4,830,006 | A | 5/1989 | Haluska et al. |
|---|---|---|---|
| 5,161,529 | A | 11/1992 | Stotts et al. |
| 5,209,229 | A | 5/1993 | Gilli |
| 5,222,493 | A | 6/1993 | Sholder |
| 5,224,475 | A | 7/1993 | Berg et al. |
| 5,251,624 | A | 10/1993 | Bocek et al. |
| 5,324,310 | A | 6/1994 | Greeninger et al. |
| 5,330,505 | A | 7/1994 | Cohen |
| 5,342,402 | A | 8/1994 | Olson et al. |
| 5,350,410 | A | 9/1994 | Kleks et al. |
| 5,472,453 | A | 12/1995 | Alt |
| 5,548,619 | A | 8/1996 | Horiike et al. |

(Continued)

FOREIGN PATENT DOCUMENTS

WO    WO-98/40122    9/1998

OTHER PUBLICATIONS

"International Search Report and Written Opinion for Application No. PCT/US01/11681, date mailed Oct. 29, 2001", 7 pgs.

*Primary Examiner*—Scott M. Getzow
(74) *Attorney, Agent, or Firm*—Schwegman, Lundberg & Woessner, P.A.

(57) ABSTRACT

A method and apparatus for delivering anti-tachycardia pacing in an adaptive manner is disclosed. A cardiac rhythm management device, such as an implantable pacemaker, having anti-tachycardia pacing capability delivers anti-tachycardia pacing therapy in accordance with a selected pacing protocol upon detection of a terminable arrhythmia. The protocol is selected from a library of available protocols. A record of the successes and failures of each available protocol in converting tachyarrhythmias is maintained in a result table for use in selecting the protocol.

20 Claims, 2 Drawing Sheets

U.S. PATENT DOCUMENTS

| | | |
|---|---|---|
| 5,587,970 A | 12/1996 | Greenwood |
| 5,662,688 A | 9/1997 | Haefner et al. |
| 5,683,424 A | 11/1997 | Brown et al. |
| 5,683,431 A | 11/1997 | Wang |
| 5,836,971 A | 11/1998 | Starkweather |
| 5,846,263 A | 12/1998 | Peterson et al. |
| 5,855,593 A | 1/1999 | Olson et al. |
| 5,871,512 A | 2/1999 | Hemming et al. |
| 5,999,854 A | 12/1999 | Deno et al. |
| 6,101,414 A | 8/2000 | Kroll |
| 6,128,529 A | 10/2000 | Elser |
| 6,137,308 A | 10/2000 | Nayak |
| 6,167,308 A | 12/2000 | DeGroot |
| 6,192,275 B1 | 2/2001 | Zhu et al. |
| 6,400,986 B1 | 6/2002 | Sun et al. |
| 6,477,422 B1 | 11/2002 | Splett |
| 2002/0058968 A1 | 5/2002 | Sun et al. |
| 2003/0083703 A1 | 5/2003 | Zhu et al. |
| 2003/0120315 A1 | 6/2003 | Spinelli et al. |
| 2005/0070967 A1 | 3/2005 | Zhu et al. |

ADAPTIVE ANTI-TACHYCARDIA THERAPY APPARATUS AND METHOD

CROSS-REFERENCE TO RELATED APPLICATION(S)

This patent application is a continuation of U.S. patent application Ser. No. 10/037,622, filed on Jan. 2, 2002, now issued as U.S. Pat. No. 6,801,806, which is a continuation of U.S. patent application Ser. No. 09/545,945, filed on Apr. 10, 2000, now issued as U.S. Pat. No. 6,400,986, the specifications of which are hereby incorporated by reference.

FIELD OF THE INVENTION

This invention pertains to methods and systems for treating cardiac arrhythmias with anti-tachycardia pacing. In particular, the invention relates to methods and systems for delivering anti-tachycardia pacing therapy with a cardiac rhythm management device.

BACKGROUND

Tachyarrhythmias are abnormal heart rhythms characterized by a rapid heart rate, typically expressed in units of beats per minute (bpm). Examples of tachyarrhythmias include supraventricular tachycardias (SVT's) such as sinus tachycardia, atrial tachycardia, and atrial fibrillation. The most dangerous tachyarrythmias, however, are ventricular tachycardia (VT) and ventricular fibrillation (VF). Ventricular rhythms occur when an excitatory focus in the ventricle usurps control of the heart rate from the sinoatrial node. The result is rapid and irregular contraction of the ventricles out of electromechanical synchrony with the atria. Most ventricular rhythms exhibit an abnormal QRS complex in an electrocardiogram because they do not use the normal ventricular conduction system, the depolarization spreading instead from the excitatory focus directly into the myocardium. Ventricular tachycardia is characterized by distorted QRS complexes occurring at a rapid rate, while ventricular fibrillation is diagnosed when the ventricle depolarizes in a chaotic fashion with no recognizable QRS complexes. Both ventricular tachycardia and ventricular fibrillation are hemodynamically compromising, and both can be life-threatening. Ventricular fibrillation, however, causes circulatory arrest within seconds and is the most common cause of sudden cardiac death.

Cardioversion (an electrical shock delivered to the heart synchronously with the QRS complex) and defibrillation (an electrical shock delivered without synchronization to the QRS complex to terminate ventricular fibrillation) can be used to terminate most tachycardias, including SVT's, VT, and VF. The electric shock terminates the tachycardia by depolarizing all excitable myocardium which prolongs refractoriness, interrupts reentrant circuits, discharges excitatory foci. A class of cardiac rhythm management devices known as an implantable cardioverter/defibrillator (ICD) provides this kind of therapy by delivering a shock pulse to the heart when fibrillation is detected by the device.

Another type of electrical therapy for tachycardia is antitachycardia pacing (ATP). In ATP, the heart is competitively paced with one or more pacing pulses in an effort to interrupt reentrant circuits causing the tachycardia. Modern ICD's typically have ATP capability so that ATP therapy is delivered to the heart when a tachycardia is detected, while a shock pulse is delivered when fibrillation occurs. Although cardioversion/defibrillation will terminate tachycardia, it consumes a large amount of stored power from the battery and results in patient discomfort owing to the high voltage of the shock pulses. It is desirable, therefore, for the ICD to use ATP to terminate a tachyarrhythmia whenever possible. Generally, only cardioversion/defibrillation will terminate fibrillation and certain high rate tachycardias, while ATP can be used to treat lower rate tachycardias. An arrhythmia which is regarded as terminable by ATP therapy, based upon rate or other factors, will be referred to herein as a terminable arrhythmia.

In most ICD's with ATP capability, ventricular fibrillation (VF) is distinguished from ventricular tachycardia (VT) using rate-based criteria so that ATP or shock therapy can be delivered as appropriate. The heart rate is usually measured by detection of the time between successive R waves (i.e., ventricular depolarizations). A measured heart rate is classified as a tachycardia when the rate is in a VT zone, defined as a range of rates above a tachycardia detection rate (TDR) but below a fibrillation detection rate (FDR). A measured heart rate above the FDR, on the other hand, is in the VF zone and is classified as a fibrillation. In a typical device, a tachycardia with a heart rate in the VT zone is treated with ATP therapy in order to avoid an unnecessary painful shock to the patient, and a defibrillation shock is delivered if the pacing fails to terminate the arrhythmia. It is a primary objective of the present invention to provide a method and apparatus for delivering ATP therapy in a manner that increases the likelihood that ATP therapy will terminate an arrhythmia without resorting to a defibrillation shock.

SUMMARY OF THE INVENTION

In accordance with the invention, a cardiac rhythm management device with ATP capability is programmed to deliver ATP therapy upon detection of a tachycardia in the VT zone by employing a pacing protocol selected from a library of such protocols. The library contains a parameter set for each protocol that defines the manner in which ATP pulses are output by the device. The selection of a particular pacing protocol from the library may be based upon information contained in a result table which reflects the past results of particular protocols in terminating arrhythmias. In one embodiment, each time a particular protocol is used in attempting to convert an arrhythmia, the success or failure of the protocol is tabulated in the result table, and a success/failure ratio is thereby maintained and associated with each protocol in the library. The device may then be programmed to select protocols from the library in an order corresponding to the success/failure ratio of each protocol in terminating an arrhythmia. A specified number of attempts with ATP therapy may made before a shock pulse is delivered, with each attempt employing a pacing protocol selected from the library in accordance with the information contained in the result table. In one embodiment, the protocol with the highest success/failure ratio is initially selected, and if the arrhythmia is not converted, the protocol with the next highest ratio is then selected. After a specified number of unsuccessful attempts with ATP therapy, a shock pulse is delivered to terminate the arrhythmia. In a further refinement of the invention, terminable arrhythmias are classified as to type based upon rate and/or the depolarization waveform morphology, and a separate result table is maintained for each type of arrhythmia. Upon detection of a particular arrhythmia type, the result table for that type is used to select the ATP protocol to be employed and is then updated with the corresponding results of the ATP therapy attempt.

In a particular embodiment, the result table is implemented with a pair of counters associated with each protocol contained in the library. After each attempt of ATP therapy using a particular protocol, the one of the counters associated with the protocol is incremented to indicate the success or failure of the protocol in terminating the arrhythmia. The information contained in the counters may then be used to calculate a success/failure ratio or some other parameter that in some way reflects the likelihood that a protocol will be successful in terminating the arrhythmia. In the case of an embodiment with separate result tables for different arrhythmia types, separate counters for each protocol are maintained for each type of arrhythmia, so that when a particular type of terminable arrhythmia is detected, the selection of the protocol is made using the counters associated with that type of arrhythmia.

DETAILED DESCRIPTION OF THE INVENTION

Figure 1:
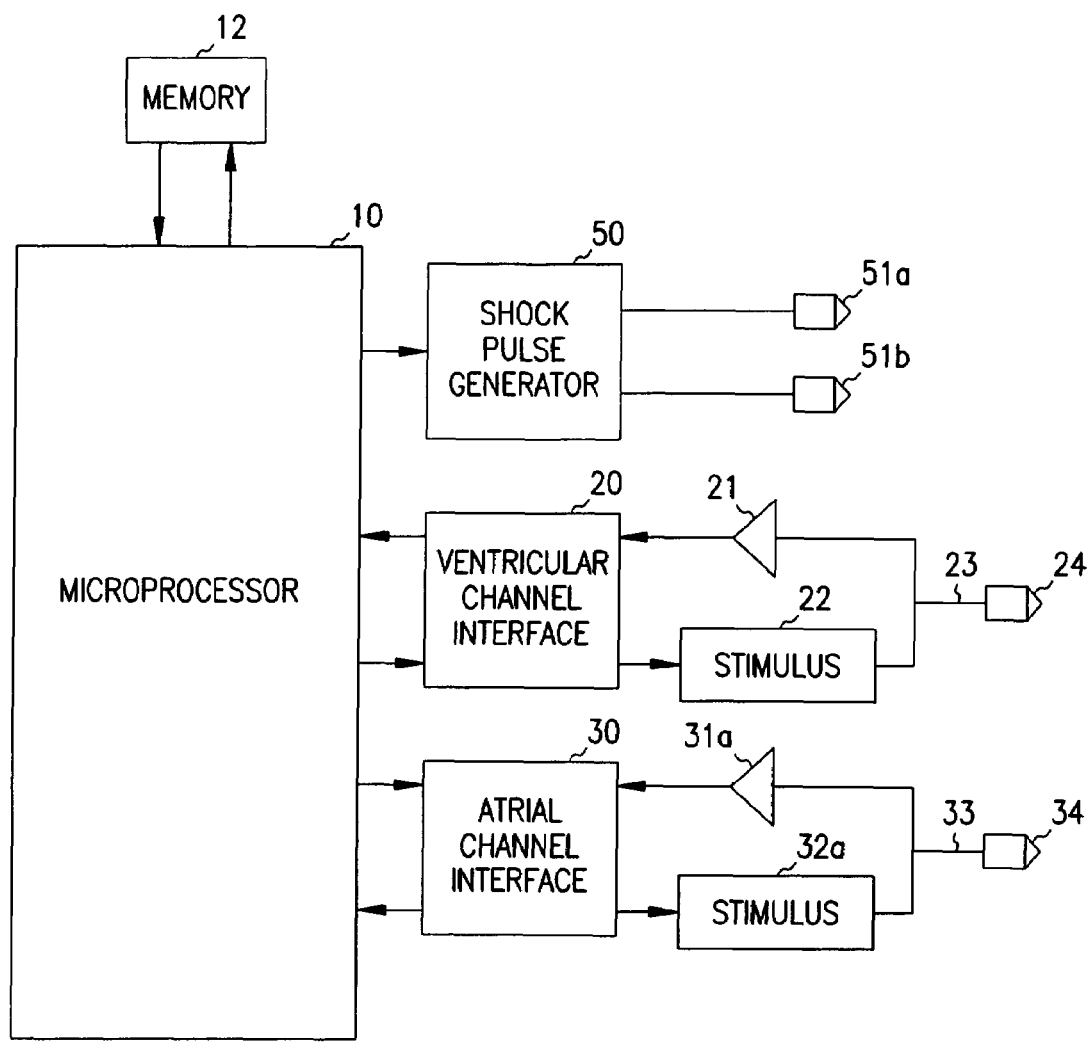
FIG. 1 is a block diagram of a cardiac rhythm management device with ATP and cardioversion/defibrillation capability.

In accordance with the invention, a cardiac rhythm management device having ATP capability is programmed with a library of pacing protocols available for delivery by the device. In a microprocessor-based device, the output of pacing pulses is controlled by a pacing routine that implements a pacing protocol as defined by various parameters. Pacing protocols for ATP therapy can generally be divided into two classes: those that deliver one or more pulses in timed relation to detected depolarizations and those that deliver a continuous pulse train for a specified time. Both types of pacing protocols attempt to reset or capture the reentrant depolarization wave front causing the tachycardia with competitive pacing pulses. Protocols of the first group may vary according to parameters that define the number of pulses delivered and the particular timing employed. Protocols of the second group include so-called burst pacing in which a short train of pulses is delivered for a specified time and may vary according to parameters that define the duration, frequency, and timing of the pulses. One type of burst pacing, called ramping, varies the frequency of the pulses up or down as the pacing is delivered. A library of pacing protocols is thus a collection of parameter sets that define these or other pacing protocols.

One way in which the library may be used is to simply program the device at the time of implantation to utilize one of the available protocols when delivering ATP therapy. Whether a given arrhythmia in the VT zone is likely to be terminated with ATP therapy, however, depends on both the design of the VT/VF zones for the detection of terminable arrhythmias and the particular pacing protocol utilized. The efficacy of a particular pacing protocol may be different, for example, for tachycardias with different heart rates. Therefore, the VT zone may be further divided into VT subzones, with a protocol selection algorithm selecting particular pacing protocols for tachycardias in different subzones. Particular pacing protocols may also be selected for application to tachycardias typed according to the morphology of the depolarization waveform. Such typing may be performed using, for example, frequency domain analysis or correlation techniques. Upon detection of a terminable arrhythmia (i.e., one deemed to be terminable by ATP therapy) of a particular type, the protocol selection algorithm can then select a particular parameter set from the library for use by the pacing routine in delivering the ATP therapy. In one implementation of an ATP protocol selection scheme, the pacing protocol is selected using a protocol selection table that associates each type of terminable arrhythmia with a protocol in the library that is regarded as most likely to be successful in terminating it. Pre-programming the protocol selection table into the device at the time of implantation, however, does not take into account that the most effective pacing protocol for a given type of arrhythmia may vary from patient to patient. Although the protocol selection table can be individualized for a given patient by testing the pacing protocols in an electro-physiology lab with induced VT's, the pacing protocols found to be most successful in terminating the induced VT's may differ markedly from the pacing protocols that would most successfully convert the spontaneous VT's that actually occur in the patient. Furthermore, putting together a pre-programmed ATP scheme requires the clinician to enter a number of interacting parameters to define the protocols and necessarily limits the number of protocols that potentially could be employed.

An improvement in accordance with the present invention is a protocol selection scheme in which ATP protocols are selected from a library in an adaptive fashion based upon a recorded history of the number of successes and failures of particular protocols in terminating detected arrhythmias. In a basic form of the invention, a list of the available protocols is maintained in the form of a table, referred to as a result table, where the results for each ATP protocol in terminating a detected terminable arrhythmia are tabulated. The result table may then be sorted in an order corresponding to the success/failure ratio of each protocol. Upon detection of terminable arrhythmia, the protocol with the highest probability of being successful, as reflected by its success/failure ratio, can then be selected from the table and used in attempting to terminate the arrhythmia. If that ATP therapy attempt fails, the next protocol in the table can be selected, with the process repeated for a specified number of times before a defibrillation shock is delivered if no ATP protocol is successful in terminating the arrhythmia. The result table is updated with the results of each ATP therapy attempt, and the table then may be re-sorted after the arrhythmia is terminated with either ATP therapy or a defibrillation shock. Alternatively, the result table may either be re-sorted after each updating of the table with a success or failure of a selected protocol or sorted at the time of each protocol selection. In an exemplary embodiment, the result table is populated with a specified number of different protocols and initialized with values corresponding to the expected probability of each protocol in terminating an arrhythmia. For example, success/failure ratio of each protocol in the result table may be set at 1:1 to reflect a 50% probability of success. The order that protocols are initially selected from the table may also be specified. After repeated ATP therapy attempts, the result table is changed to reflect the actual operating experience of the device in terminating arrhythmias and re-sorted in accordance therewith. A system incorporating the present invention is thus able to learn which protocols are the most successful in terminating arrhythmias.

The same adaptive protocol selection scheme described above may also be employed to select particular protocols for particular types of detected arrhythmias. In such an embodiment, separate result tables are maintained for each type of terminable arrhythmia classified with respect to rate and/or waveform morphology. Each result table can be populated with protocols selected specifically for a particular arrhythmia type. Then upon detection of a particular type of arrhythmia, an ATP protocol is selected from the result table for that arrhythmia type, and an attempt is made to terminate the arrhythmia with that protocol. The results are recorded in the result table for the detected arrhythmia type as a success or failure after each ATP therapy attempt, and the table is re-sorted after termination of an arrhythmia.

In the description that follows, a microprocessor-based cardiac rhythm management device will be referred to as incorporating the system and method that is the present invention. In the embodiment to be described, the invention is implemented with a control unit made up of a microprocessor executing programmed instructions in memory. It should be appreciated, however, that certain functions of a cardiac rhythm management device can be controlled by custom logic circuitry either in addition to or instead of a programmed microprocessor. The term "control unit" as used herein should therefore be taken to encompass either custom circuitry (i.e., dedicated hardware) or a microprocessor executing programmed instructions contained in a processor-readable storage medium along with associated circuit elements.

FIG. 1 is a system diagram of a microprocessor-based cardiac rhythm management device with the capability of delivering cardioversion/defibrillation shocks as well as antitachycardia pacing therapy. The device may also be configured to deliver conventional (e.g., bradycardia) pacing as well. The control unit of the device is a microprocessor 10 that communicates with a memory 12 via a bidirectional data bus. The memory 12 typically comprises a ROM for program storage and a RAM for data storage. The pacing routine, protocol selection algorithm, the protocol library, the result tables The device has atrial sensing and pacing channels comprising electrode 34, lead 33, sensing amplifier 31a, pulse generator 32a, and an atrial channel interface 30 which communicates bidirectionally with a port of microprocessor 10. The ventricular sensing and pacing channels similarly comprise electrode 24, lead 23, sensing amplifier 21, pulse generator 22, and a ventricular channel interface 20. For each channel, the same lead and electrode are used for both sensing and pacing. The sensing and pacing channels are used for anti-tachycardia pacing and for measuring heart rate in order to detect tachycardia and fibrillation. The microprocessor 10 analyzes the signals received from the sensing channels to detect and type arrhythmias and controls the operation of the pacing channels in order to deliver ATP therapy in accordance with a selected protocol. A shock pulse generator 50 is also interfaced to the microprocessor for delivering cardioversion or defibrillation pulses to the heart via a pair of electrodes 51a and 51b.

The device delivers ATP therapy or a defibrillation shock under programmed control of the microprocessor in response to sensed activity from the sensing channels. A sensing routine analyzes the electrical activity received from the sensing channels in order to detect an arrhythmia, and the arrhythmia is then classified as a tachycardia (i.e., a terminable arrhythmia) or fibrillation based upon rate. The device detects a ventricular tachyarrhythmia, for example, by measuring a heart rate via the ventricular sensing channel and determining whether the rate exceeds a selected threshold value. Once a tachyarrhythmia is detected, the rhythm is classified into either a tachycardia or a fibrillation by comparing the heart rate to a fibrillation rate boundary. A detected VT, for example, may then be further classified as to type by VT subzone and/or waveform morphology. The detected depolarization waveform morphology is analyzed by correlation or frequency domain techniques in order to classify the morphology of waveform. For example, a ventricular rhythm detected in the fibrillation zone may nonetheless be regarded as a terminable VT if the waveform morphology indicates that the arrhythmia is a VT and not a fibrillation.

If the arrhythmia is classified as terminable, a pacing routine executed by the microprocessor controls the output of ATP pulses in accordance with protocol parameters stored in the protocol library. The protocol library is a data structure in memory containing a plurality of pacing parameter sets, each of which is accessible by the pacing routine using a protocol identifier. For each terminable arrhythmia type that is to be detectable by the device, one or more pacing protocols are designated as available for use by the pacing routine in attempting to terminate the arrhythmia with ATP therapy. For each terminable arrhythmia type, a result table is defined in memory that contains a list of the identifiers for the designated protocols. The result table is a data structure that is used to record the successes and failures of a protocol in terminating detected arrhythmias so that the protocol with the greatest probability of terminating an arrhythmia can be selected for the ATP therapy attempt. One way of implementing this is to maintain a count of the number of successes and failures of each protocol in terminating arrhythmias with a pair of counters associated with each protocol. A success/failure ratio can be calculated for each protocol in the table, and the result table can then be sorted on the basis of the success/failure ratio so that protocols can be selected from the table in order upon detection of a terminable arrhythmia. Alternatively, the table can be searched for the protocol identifier with the highest ratio whenever a protocol is to be selected. Thus when a terminable arrhythmia is detected and typed, a protocol selection routine selects a protocol identifier from that type's result table with the highest success/failure ratio. The pacing routine then uses the selected identifier to access a parameter set from the protocol library and deliver ATP therapy employing those parameters. The result table is updated after each delivery ATP therapy by incrementing one of the counters associated with the particular protocol employed. If the therapy is successful in terminating the arrhythmia, the device returns to a monitoring mode. If the arrhythmia is not terminated, the protocol identifier with the next highest success/failure ratio is selected from the result table, either by searching the table or selecting the next identifier in a sorted table, and ATP therapy is tried again with the new protocol. If the arrhythmia is still not converted, the process can be repeated a specified number of times before a defibrillation shock is employed.

Figure 2:
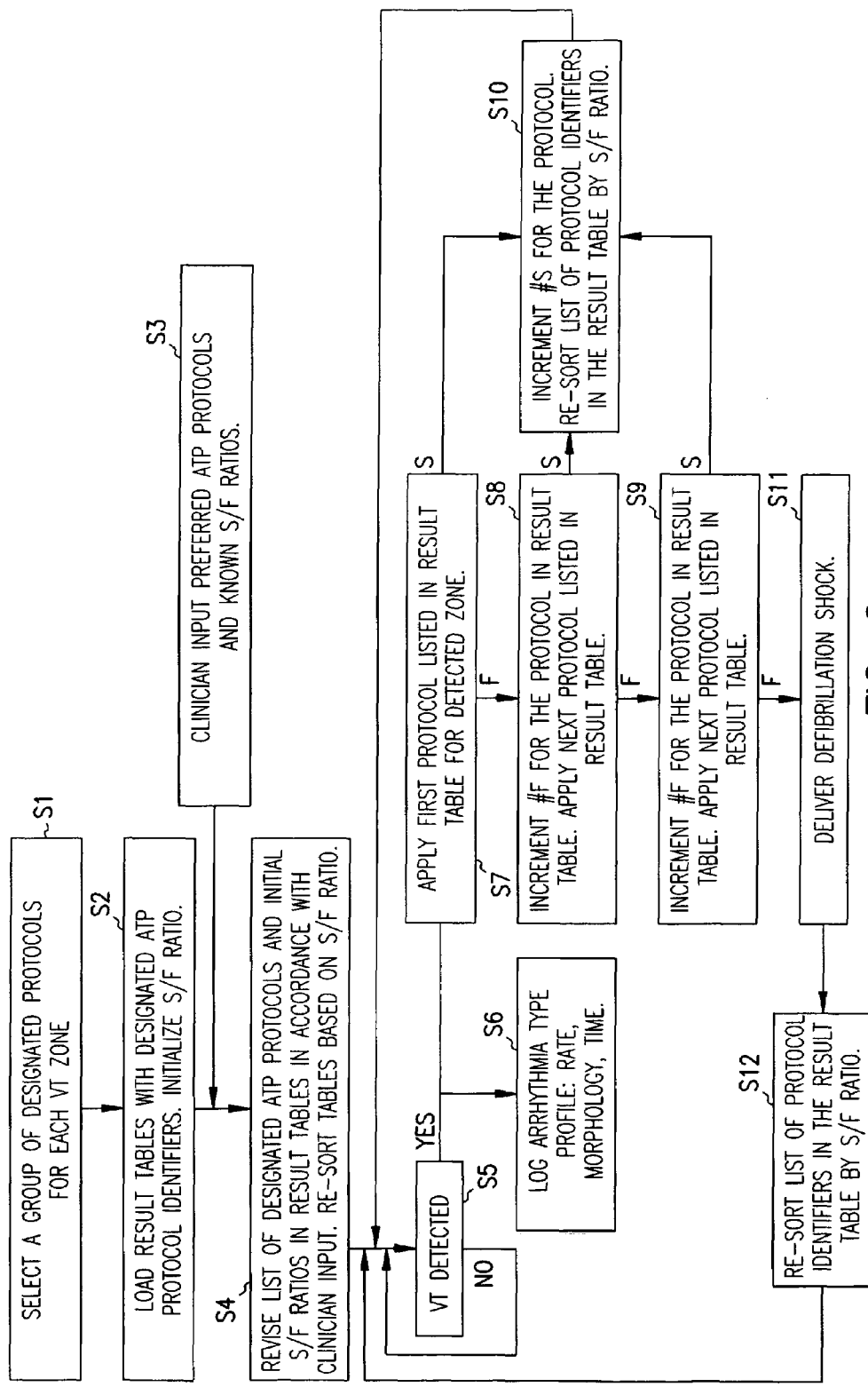
FIG. 2 is a flow diagram showing the steps performed in one implementation of the present method.

FIG. 2 shows a flow diagram of the steps performed in one particular implementation of the invention for the detection and treatment of ventricular arrhythmias. Steps S1 through S4 are configuration steps involved in setting up the device for operation, while steps S5 through S12 are performed by the microprocessor under programmed control. At step S1, a group of ATP protocols are designated for each VT subzone (i.e., arrhythmia type). The corresponding identifiers for the designated protocols are then stored in the result tables for each VT subzone at step S2, and the S/F (success/failure) ratios are initialized. A clinician may input a different choice of designated protocols for each VT subzone as well as the initial S/F ratio values at step S3. At step S4 in this embodiment, the list of protocols in the result tables and S/F ratios are revised in accordance with clinician input, and the list for each VT subzone is re-sorted based on the S/F ratio. Monitoring for terminable arrhythmias is performed at step S5. If a VT is detected, it is typed as falling within a particular VT subzone, and an arrhythmia profile is logged at step S6. The ATP protocol at the top of the list in the result table for the detected VT subzone is selected and applied at step S7. If the ATP therapy with the selected protocol fails to terminate the arrhythmia, the failure counter for that protocol is incremented at step S8, and the next protocol listed in the result table is selected and applied. If the attempt at ATP therapy with the new protocol also fails, the failure counter for that protocol is incremented, and another protocol is selected from the list and applied at step S9. If that ATP therapy attempt fails, a defibrillation shock is delivered at step S11. If the arrhythmia is successfully terminated at any of the steps S7 through S9, the success counter for the protocol employed is incremented at step S10, the protocol list in the result table is re-sorted based on S/F ratios, and the system returns to monitoring at step S5. The protocol list is also re-sorted at step S12 after termination of an arrhythmia by a defibrillation shock before returning to monitoring.

Although the invention has been described in conjunction with the foregoing specific embodiment, many alternatives, variations, and modifications will be apparent to those of ordinary skill in the art. Such alternatives, variations, and modifications are intended to fall within the scope of the following appended claims.

What is claimed is:

1. A method for delivery of anti-tachycardia pacing (ATP) therapy by a cardiac rhythm management device, comprising:
   monitoring cardiac electrical activity in order to detect an arrhythmia;
   upon detection of a terminable arrhythmia, selecting a first pacing protocol for delivering ATP therapy from a list of possible protocols, wherein the selection is based upon a record of the protocols in terminating prior arrhythmias;
   delivering ATP therapy in accordance with the selected first protocol;
   recording whether the first protocol was unsuccessful in terminating the arrhythmia; and,
   selecting a second protocol if the first protocol was unsuccessful in terminating the arrhythmia;
   delivering ATP therapy in accordance with the second protocol; and,
   recording whether the second protocol was unsuccessful in terminating the arrhythmia.

2. The method of claim 1 further comprising continuing to select a next protocol from the list of possible protocols and delivering ATP therapy in accordance with the selected next protocol if the previous protocol was unsuccessful in terminating the arrhythmia.

3. The method of claim 1 further comprising recording whether each selected protocol was successful in terminating an arrhythmia.

4. The method of claim 1 further comprising classifying a detected arrhythmia as to type and selecting a protocol from the list with the highest probability of terminating that arrhythmia type.

5. The method of claim 4 wherein a protocol for delivering ATP therapy is selected from the list in accordance with a recorded success/failure ratio specific for the type of arrhythmia detected.

6. The method of claim 5 further comprising updating the success/failure ratio specific for the type of arrhythmia detected in accordance with the success or failure of the protocol in terminating the arrhythmia.

7. The method of claim 6 wherein each success/failure ratio associated with each protocol in the list is initialized to 1:1.

8. The method of claim 4 wherein the arrhythmia type is based upon waveform morphology.

9. The method of claim 4 wherein the arrhythmia type is based upon rate.

10. The method of claim 1 further comprising delivering a defibrillation shock if a specified number of ATP therapy attempts are unsuccessful in terminating the arrhythmia.

11. A cardiac rhythm management device, comprising:
    a sensing and pacing channel for sensing cardiac electrical activity and delivering pacing pulses;
    a shock pulse generator for delivering a defibrillation shock;
    a control unit for detecting a terminable arrhythmia and delivering ATP therapy; and,
    wherein the control unit is programmed to:
    upon detection of a terminable arrhythmia, select a first pacing protocol for delivering ATP therapy from a list of possible protocols, wherein the selection is based upon a record of the protocols in terminating prior arrhythmias;
    deliver ATP therapy in accordance with the selected first protocol;
    record whether the first protocol was unsuccessful in terminating the arrhythmia; and,
    select a second protocol if the first protocol was unsuccessful in terminating the arrhythmia;
    deliver ATP therapy in accordance with the second protocol; and,
    record whether the second protocol was unsuccessful in terminating the arrhythmia.

12. The device of claim 11 wherein the controller is further programmed to continue to select a next protocol from the list of possible protocols and delivering ATP therapy in accordance with the selected next protocol if the previous protocol was unsuccessful in terminating the arrhythmia.

13. The device of claim 11 wherein the controller is further programmed to record whether each selected protocol was successful in terminating an arrhythmia.

14. The device of claim 11 wherein the controller is further programmed to classify a detected arrhythmia as to type and select a protocol from the list with the highest probability of terminating that arrhythmia type.

15. The device of claim 14 wherein the controller is programmed to select a protocol for delivering ATP therapy from the list in accordance with a recorded success/failure ratio specific for the type of arrhythmia detected.

16. The device of claim 15 wherein the controller is further programmed to update the success/failure ratio specific for the type of arrhythmia detected in accordance with the success or failure of the protocol in terminating the arrhythmia.

17. The device of claim 16 wherein each success/failure ratio associated with each protocol in the list is initialized to 1:1.

18. The device of claim 14 wherein the arrhythmia type is based upon waveform morphology.

19. The device of claim 14 wherein the arrhythmia type is based upon rate.

20. The device of claim 11 wherein the controller is further programmed to deliver a defibrillation shock if a specified number of ATP therapy attempts are unsuccessful in terminating the arrhythmia.

* * * * *